United States Patent
Forssmann et al.

(10) Patent No.: US 6,831,064 B1
(45) Date of Patent: Dec. 14, 2004

(54) USE OF URODILATIN FOR TREATING CHRONIC KIDNEY FAILURE WITH RESIDUAL KIDNEY FUNCTIONS

(75) Inventors: Wolf-Georg Forssmann, Hannover (DE); Kristin Forssmann, Hannover (DE); Wolfgang Greb, Düsseldorf (DE); Markus Meyer, Hannover (DE)

(73) Assignee: Pharis Biotec GmbH, Hannover (DE)

( * ) Notice: Subject to any disclaimer, the term of this patent is extended or adjusted under 35 U.S.C. 154(b) by 29 days.

(21) Appl. No.: 10/088,498

(22) PCT Filed: Oct. 24, 2000

(86) PCT No.: PCT/EP00/10462

§ 371 (c)(1),
(2), (4) Date: Jul. 18, 2002

(87) PCT Pub. No.: WO01/30376

PCT Pub. Date: May 3, 2001

(30) Foreign Application Priority Data

Oct. 24, 2000 (DE) .......................................... 199 51 471

(51) Int. Cl.⁷ ............................................... A61K 38/00
(52) U.S. Cl. ......................................................... 514/12
(58) Field of Search ............................................ 514/12

(56) References Cited

U.S. PATENT DOCUMENTS

| 5,565,428 A | * 10/1996 | Clark et al. ..................... 514/12 |
| 5,571,789 A | * 11/1996 | Fl uge et al. .................. 514/12 |
| 5,691,310 A | 11/1997 | Vesely |

FOREIGN PATENT DOCUMENTS

| WO | WO 88/06596 | 2/1988 | |
| WO | 88/06596 | * 9/1988 | .......... A61K/37/24 |

OTHER PUBLICATIONS

Meyer et al. Urodilatin, a natriuretic peptide with clinical implications. Eur J Med Res. Feb. 21, 1998; 3(1–2):103–110. Review.*

Seeman et al. "Urinary excretion of urodilatin in healthy children and children with renal disease", XP–000993239, Pediatric Nephrology, (1998) pp. 55–59.

Meyer et al. "Urodilatin, A Natriuretic Peptide with Clinical Implications", XP–000993049, European Journal of Medical Research, (1998), pp. 103110.

* cited by examiner

*Primary Examiner*—Christopher R. Tate
*Assistant Examiner*—Maury Audet
(74) *Attorney, Agent, or Firm*—Jacobson Holman PLLC

(57) ABSTRACT

Use of urodilatin for treating chronic renal insufficiency by stimulating the residual renal function.

2 Claims, No Drawings

USE OF URODILATIN FOR TREATING CHRONIC KIDNEY FAILURE WITH RESIDUAL KIDNEY FUNCTIONS

This is a 371 of PCT/EP00/10462, filed Oct. 24, 2000, the disclosure of which is incorporated herein by reference.

The present invention relates to the use of urodilatin for treating chronic renal insufficiency with residual renal function.

Urodilatin is a peptide which is the subject matter of European Patent EP-A-0 349 545. This Patent Specification also mentions indications of urodilatin in which urodilatin is to be employed in renal insufficiency.

Patients suffering from chronic renal insufficiency go through different stages of treatment as the disease progresses:

a) promotion of residual renal function;

b) hemodialysis or peritoneal dialysis; and, if possible c) kidney transplantation.

In step a), hemodialysis or peritoneal dialysis is not yet necessary. Thus, it is sought to maintain this stage as long as possible even with a negative prognosis in order to save a patient with renal insufficiency from dialysis as long as possible. Surprisingly, urodilatin can be employed for prolonging phase a). Urodilatin, being an endogenous product, has an activity profile with a synergistic effect of particular importance: In the kidney, diuresis and natriuresis lead to the mobilization of fluids and thus to the clearance of urinary waste substances through an increase of the glomerular filtration rate (GFR) and inhibition of sodium reabsorption. Due to the simultaneous intrarenal vascular dilatation, urodilatin has a kidney-protecting effect as has now been found.

Thus, the present invention relates to the use of urodilatin for treating chronic renal insufficiency with residual renal function.

According to the invention, an improvement of residual renal function can be used in patients with chronic renal insufficiency before obligatory dialysis, and/or for prolonging the dialysis-free intervals in patients with chronic renal insufficiency. In particular, the latter alternative is also of great importance to the afflicted patients, because the frequency of dialysis can be reduced thereby.

In EP-A-0 349 545, various clinical indications were mentioned in which urodilatin is employed as an intravenous infusion. These include acute renal insufficiency, inter alia.

The amount of urodilatin to be used according to the invention is from 5 ng/kg of body weight to 10 $\mu$g/kg of body weight. The skilled person known that these ranges serve as clues for establishing an optimum dosage. Of course, the minimum possible amount to be administered is that which is just above the threshold value of a detectable effect, whereas the upper limit is determined by toxic phenomena occurring. Typically, the dosages are within the stated range.

Especially the applications of urodilatin as an intravenous infusion in a dosage of, for example, 20 mg/kg of body weight/min, especially over a period of from 6 to 24 hours, in patients with chronic preterminal renal insufficiency which is not yet subject to obligatory dialysis result in an increased clearance of fluid and urinary waste substances.

In addition, also as an intravenous infusion between the dialysis intervals, urodilatin results in a stimulation of residual renal function and thus in an increased clearance of fluid and urinary waste substances. Thus, urodilatin is particularly suitable for improving the residual renal function in a stage before obligatory dialysis and causes obligatory dialysis to be delayed. In addition, urodilatin is suitable as a medicament for use between dialyses to prolong the dialysis-free intervals.

The use of urodilatin according to the invention for improving the clearance of fluid and urinary waste substances into the abdominal cavity in patients with chronic renal insufficiency is performed by adding the urodilatin to the peritoneal dialysate of patients with chronic renal insufficiency.

The therapy of chronic terminal renal insufficiency consists in hemodialysis and peritoneal dialysis. In peritoneal dialysis, the clearance of fluid and urinary waste substances is controlled by the peritoneal dialysate administered into the abdominal cavity, which consists of sugars and electrolytes.

Surprisingly, the administration of urodilatin according to the invention virtually as an additive to the peritoneal dialysate causes an enhanced clearance of fluid and urinary waste substances into the abdominal cavity. Thus, urodilatin may also be used as a medicament in patients with chronic terminal renal insufficiency.

What is claimed is:

1. A method of treating chronic renal insufficiency comprising administering an effective amount of urodilatin to a patient with chronic renal insufficiency for one or both of (i) improving residual renal function in the patient before obligatory dialysis and (ii) prolonging the patient's dialysis-free intervals.

2. A method of treating chronic renal insufficiency comprising adding an effective amount of urodilatin to the peritoneal dialysate of a patient with chronic renal insufficiency undergoing dialysis, for improving the clearance of fluid and urinary waste substances into the abdominal cavity of the patient.

* * * * *